(12) United States Patent
Stelting et al.

(10) Patent No.: US 7,363,158 B2
(45) Date of Patent: Apr. 22, 2008

(54) METHOD FOR CREATING A STRATIGRAPHIC MODEL USING PSEUDOCORES CREATED FROM BOREHOLE IMAGES

(75) Inventors: Charles E. Stelting, Missouri, TX (US); William J. Schweller, Walnut Creek, CA (US); William C. Corea, San Ramon, CA (US); William H. Crane, San Ramon, CA (US); Lisa R. Goggin, Sugar Land, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 218 days.

(21) Appl. No.: 11/399,969

(22) Filed: Apr. 7, 2006

(65) Prior Publication Data

US 2007/0239359 A1 Oct. 11, 2007

(51) Int. Cl.
  G01V 1/04 (2006.01)
  G01N 15/08 (2006.01)
(52) U.S. Cl. .......................................... 702/6; 702/12
(58) Field of Classification Search ................ 702/1–8, 702/12; 703/1–10
See application file for complete search history.

(56) References Cited

U.S. PATENT DOCUMENTS 4,821,164 A * 4/1989 Swanson ........................ 702/5
5,838,634 A * 11/1998 Jones et al. .................... 367/73

OTHER PUBLICATIONS

Bourke, Sedimentological borehole image analysis in clastic rocks: a systematic approach to interpretation, Geological Applications of Wireline Logs II, 1992, pp. 31-42, Geological Society Special Publication No. 65, The Geological Society, London.

Harker et al., Methodology of Formation MicroScanner image interpretation in Claymore and Scapa Fields (North Sea), Geological Applications of Wireline Logs II, 1990, pp. 11-25, Geological Society Special Publication No. 48, The Geological Society, London.

Jaramillo et al., B-14 True Amplitude Migration and Dip Equalisation, EAGE 62nd Conference and Technical Exhibition, May 29-Jun. 2, 2000, Glasgow, Scotland.

(Continued)

*Primary Examiner*—John Barlow
*Assistant Examiner*—Victor Jackson Taylor
(74) *Attorney, Agent, or Firm*—Richard J. Schulte; Maurice E. Teixeira (57) ABSTRACT

A method for creating a stratigraphic model is provided. A core is obtained from a wellbore and a detailed graphic core description is created. Wireline data, including a borehole image, is obtained for a cored interval corresponding to the core and processed into an interpretable borehole image. The core description is compared with the interpretable borehole image to create a catalogue of geologic image facies. The borehole image from the entire interval of interest is compared to the catalogue to create a preliminary pseudocore description. The interpretable borehole image is interactively examined and compared with the preliminary pseudocore description to create a master pseudocore interpretation. A second master pseudocore is developed for a second wellbore. A stratigraphic model, and subsequently a reservoir model, may then be created by correlating between the master pseudocores of the first and second wellbores.

11 Claims, 6 Drawing Sheets

OTHER PUBLICATIONS

King, Incorporating geological data in well log interpretation, Geological Applications of Wireline Logs, 1990, pp. 45-55, Geological Society Special Publication No. 48, The Geological Society, London.

Luthi, Sedimentary structures of clastic rocks identified from electrical borehole images, Geological Applications of Wireline Logs, 1990, pp. 3-10, Geological Society Special Publication No. 48, The Geological Society, London.

Luthi, Geological Well Logs, Their Use in Reservoir Modeling, 2001, pp. 74-123, ISBN 3-540-67840-9, Springer-Verlag, Berlin Heidelberg New York.

Luthi, Geological Well Logs, Their Use in Reservoir Modeling, 2001, pp. 258-297, ISBN 3-540-67840-9, Springer-Verlag, Berlin Heidelberg New York.

Luthi, Geological Well Logs, Their Use in Reservoir Modeling, 2001, pp. 330-341, ISBN 3-540-67840-9, Springer-Verlag, Berlin Heidelberg New York.

Prosser et al., Methodologies for multi-well sequence analysis using borehole image and dipmeter data, Borehole Imaging: applications and case histories, 1999, pp. 91-121, Geological Society Special Publication No. 159, The Geological Society, London.

Ye et al., Automatic High Resolution Sedimentary Dip Detection on Borehole Imagery, Society of Professional Well Log Analysts 38th Annual Logging Symposium, Jun. 15-18, 1997, pp. 1-13, Paper O.

Ye et al., Automatic High Resolution Texture Analysis on Borehole Imagery, Society of Professional Well Log Analysts 39th Annual Logging Symposium, May 26-29, 1998, pp. 1-14, Paper M.

Ye et al., A New Tool for Electro-Facies Analysis Multi-Resolution Graph-Based Clustering, Society of Professional Well Log Analysts 41st Annual Logging Symposium, Jun. 4-7, 2000, pp. 1-14, Paper PP.

Zeh et al., Neural Applications to Geological and Petrophysical Data for Improved Flow-Unit Identification, Society of Professional Well Log Analysts European Symposium, 2002, pp. 1-12, Paper T2C.

* cited by examiner

Step 140: Processing Wireline Data into Interpretable Borehole Images

Step 150: Create Detailed Core to OBMI Comparison

METHOD FOR CREATING A STRATIGRAPHIC MODEL USING PSEUDOCORES CREATED FROM BOREHOLE IMAGES

TECHNICAL FIELD

The present invention relates generally to stratigraphic modeling of subterranean reservoirs, and more particular, to a method for establishing fine-scale stratigraphic correlation and reservoir continuity using a combination of cores and borehole images obtained from nearby wellbores.

BACKGROUND OF THE INVENTION

For appropriate development of a reservoir model of a hydrocarbon reservoir, detailed stratigraphic models and information are required to predict the character of the reservoir between wellbores. Regular wireline logs from the wellbores do not provide sufficient detail. Conventional cores provide the necessary detail, but are limited in extent and are very expensive. Previous work on stratigraphic interpretation from borehole images has been restricted to one-well-at-a-time efforts and has not been carefully calibrated to cores.

There is a need for a method for creating a more detailed stratigraphic model which relies upon borehole images and core information obtained from wellbores which are located near one another in a field.

SUMMARY OF THE INVENTION

A method for creating a stratigraphic model is provided. A conventional core is obtained from a wellbore. The wellbore includes an interval of stratigraphic interest which includes a cored interval from which the core was obtained. The core is examined and a graphic core description is developed from the examination.

Wireline data is obtained from the interval of stratigraphic interest. The wireline data includes a borehole image and, preferably, a suite of well logs. The wireline data is processed into an interpretable borehole image. The detailed graphic core description is compared with a portion of the borehole image corresponding to the cored interval to create a catalogue of geologic image facies. The entire borehole image is compared with the catalogue of geologic image facies to create a preliminary pseudocore for the interval of stratigraphic interest. Next, the interpretable borehole image and the preliminary pseudocore are compared to create a master pseudocore.

Second wireline data is obtained from a second wellbore and covers a second interval of stratigraphic interest. The second wireline data includes a second borehole image and, preferably, a suite of well logs. The second wireline data is processed into a second interpretable borehole image. This second borehole image is compared to the catalogue of geologic image facies to create a second preliminary pseudocore for the second interval of stratigraphic interest. The second interpretable borehole image is examined with the second preliminary pseudocore and a second master pseudocore is created. The first and second master pseudocores are then correlated between the wellbores to create a stratigraphic model. Optionally, a reservoir model may be built from the stratigraphic model.

It is an object to provide a method for establishing fine-scale stratigraphic correlation and reservoir continuity using a combination of cores and borehole image data from a plurality of nearby wellbores.

It is another object to provide a method for creating a detailed stratigraphic interpretation of a wellbore without cores by assigning geologic image facies derived from a different wellbore.

BRIEF DESCRIPTION OF THE DRAWINGS

These and other objects, features and advantages of the present invention will become better understood with regard to the following description, pending claims and accompanying drawings where:

DETAILED DESCRIPTION OF THE INVENTION

The present invention provides a method for creating a stratigraphic model from borehole image data and one or more cores. Subsequently, a reservoir model may be made from the stratigraphic model.

Figure 1:
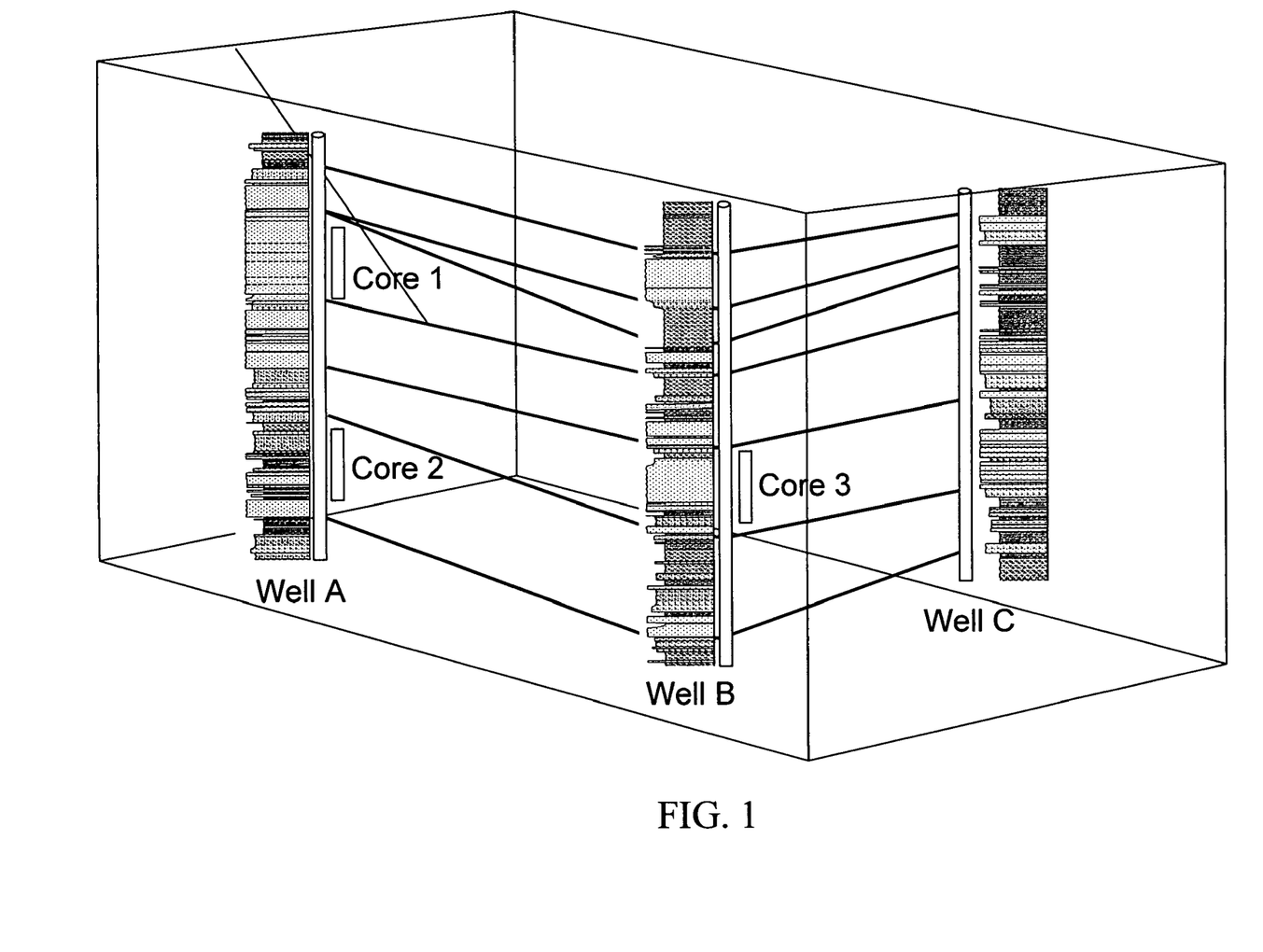
FIG. 1 is a schematic illustration of a 3-dimensional reservoir model made in accordance with the present invention which has three exemplary pseudocores which are correlated between wellbores to create a stratigraphic model.

FIG. 1 shows a 3-dimensional reservoir model which contains wellbores A, B, and C. Geologic interpretations or "master pseudocores" are shown adjacent each of the wellbores. The master pseudocores are based upon borehole images calibrated across one or more cored intervals. The three cores are associated with cored intervals in the wellbores. Connecting lines illustrate the correlation of reservoir zones or facies between pairs of wellbores.

Figure 2:
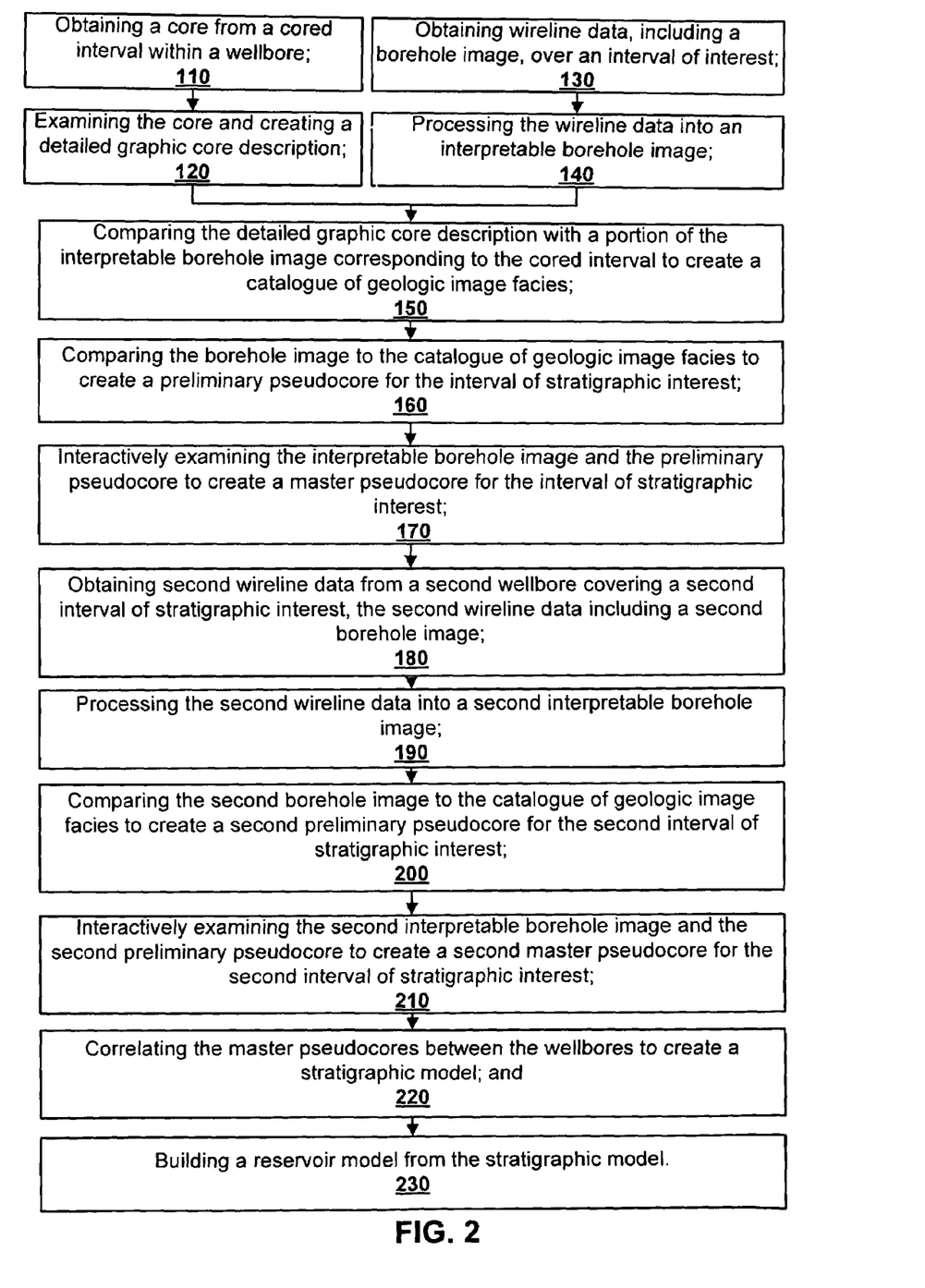
FIG. 2 is a flowchart of a preferred embodiment of a method used in constructing the stratigraphic model of FIG. 1.

FIG. 2 is a flowchart which describes the steps taken in an exemplary method of constructing a stratigraphic model. First, a core is obtained in step 110 from a cored interval within a wellbore. The core is examined and a detailed graphic core description is created in step 120. Wireline data is then obtained in step 130 over an interval of stratigraphic interest of the wellbore which also contains the cored interval. The cored interval is generally much smaller in length than the overall interval of stratigraphic interest of the wellbore for which additional stratigraphic information is sought. The wireline data includes a borehole image. This wireline data is then processed in step 140 into an interpretable borehole image.

The detailed graphic core description is compared with the portion of the interpretable borehole image which corresponds to the cored interval. Subsequently, a catalogue of geologic image facies is created in step 150. This catalogue of geologic image facies is then compared against the borehole image in step 160 to create a preliminary pseudocore for the interval of stratigraphic interest. A workstation is preferably used in step 170 to interactively examine the interpretable borehole image and the preliminary pseudocore for the interval of stratigraphic interest to create a master pseudocore.

Second wireline data is obtained in step 180 from a second wellbore which covers a second interval of stratigraphic interest. The second wireline data includes a second borehole image. The second wireline data is processed into a second interpretable borehole image in step 190. The second borehole image is compared in step 200 with the catalogue of geologic image facies to create a second preliminary pseudocore for the second interval of stratigraphic interest. The second interpretable borehole image is examined in step 210, preferably interactively with a computer workstation, to create a second master pseudocore for the second interval of stratigraphic interest. The master pseudocores are correlated between the wellbores to create a stratigraphic model in step 220. This stratigraphic model may then be used in building a reservoir model in step 230.

Optionally, more than one core may be used in developing an enhanced catalogue of geologic image facies. Detailed graphic core descriptions for these additional cores are compared with corresponding portions of interpretable borehole images to create the enhanced catalogue of geologic image facies. Again, this enhanced catalogue of geologic image facies is compared against borehole images to create preliminary pseudocores. The additional cores may come from first wellbore, the second wellbore, or both. The above method may be extended such that a correlation is done between a number of wellbores in constructing the stratigraphic model. The stratigraphic model is preferably a 3-dimensional model as is the reservoir model. However, the present method may also be useful in constructing 2-dimensional models.

The aforementioned steps in constructing the stratigraphic model shall now be described in greater detail.

Step 110: Obtaining Cores

Cores are taken from one or more intervals of interest in at least one of the wellbores A, B or C. Referring to FIG. 1, two spaced apart cores and cored intervals are shown in wellbore A and a third core is shown in wellbore B. In this example, no cores are taken from wellbore C. Core information from wellbores A and B can be extrapolated to wellbore C, as will be described below. Corresponding to each of the cores is a cored interval in the respective wellbore from which the core was obtained. It is possible to utilize this method with only one core. However, more preferably, cores would be taken from each of the wellbores. Further, ideally one core would be taken from each reservoir zone in each wellbore. Typically, the cores are of 100-200 feet in length and 4-6 inches in diameter. As mentioned above, the cores contribute to creating the overall catalogue of geologic image facies.

Step 120: Examining Core(s) and Creating Detailed Graphic Core Descriptions

Figure 3A:
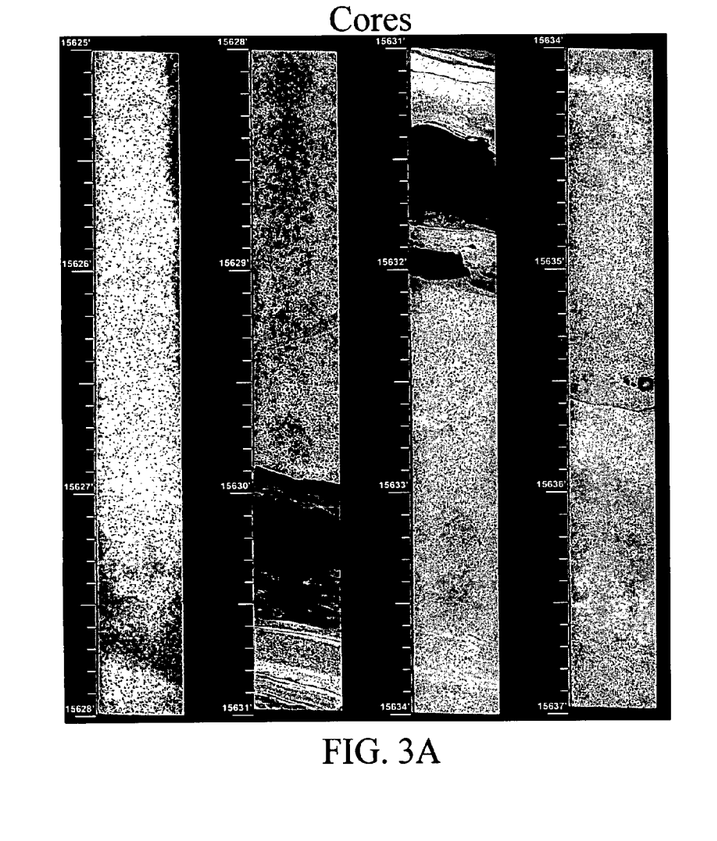
FIG. 3A shows a core, split into four segments.
Figure 3B:
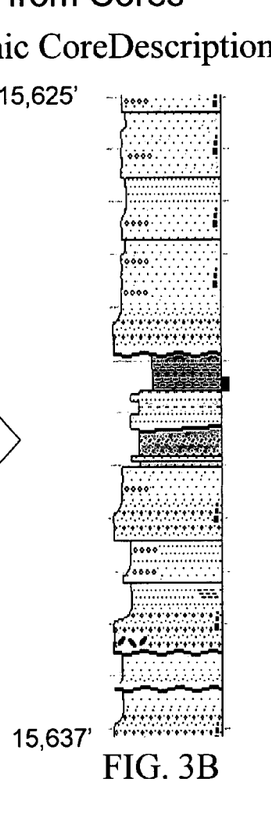
FIG. 3B illustrates a continuous detailed graphic core description of the core.

The core from step 110 is examined and a detailed graphic core description is developed. FIG. 3A shows four adjacent and distinct segments of a core. Typically, each of the segments is approximately three feet in length. FIG. 3B illustrates a continuous detailed graphic core description corresponding to the four segments of core. The graphic core description consists of a graphic summary of physical characteristics of the core. By way of example, and not limitation, these characteristics may include lithology, grain size, physical structures and other attributes of the core. The process of creating a detailed graphic core description from an interval of core is well known to those skilled in the art of examining geologic data from wells and will not be described in further detail.

Step 130: Obtaining Wireline Data Including Borehole Image Data

Wireline data is next obtained for the wellbore over an interval of stratigraphic interest. This interval of stratigraphic interest contains the smaller cored interval from which the core was extracted. Typically, these intervals of stratigraphic interest are of approximately 1000 to 5000 feet in length. Accordingly, this interval of interest is many times the length of the cored interval.

Wireline data is obtained by running a wireline tool down the wellbore of interest. The wireline data obtained may include, by way of example and not limitation, borehole image data and at least a minimal suite of conventional well logs (gamma ray, density, sonic, neutron, caliper, porosity, etc). This data is preferably gathered in a digital format. A preferred image tool is Oil Based Micro Imager (OBMI)™ commercially available from Schlumberger Information Solutions of Houston, Tex. Those skilled in the art will appreciate that other types of imaging may be used as well with the present invention.

Step 140: Processing Wireline Data into Interpretable Borehole Images

Figure 4A:
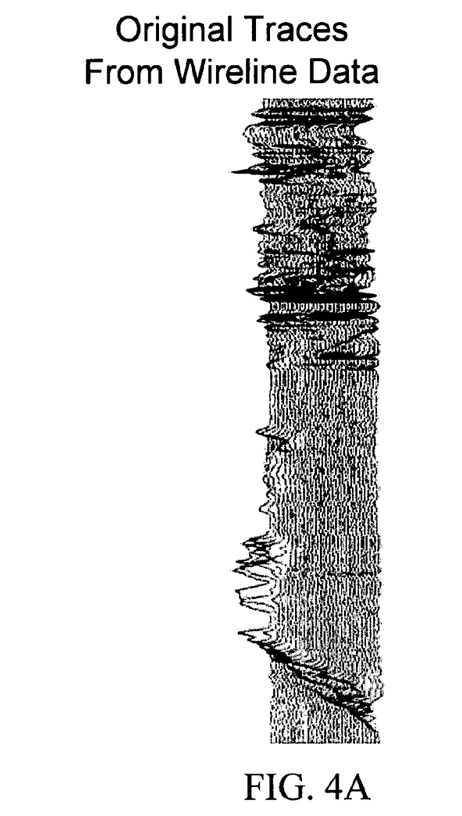
FIGS. 4A and 4B, respectively, show original traces from wireline data and a segment of an interpretable borehole image which was made from the wireline data.
Figure 4B:
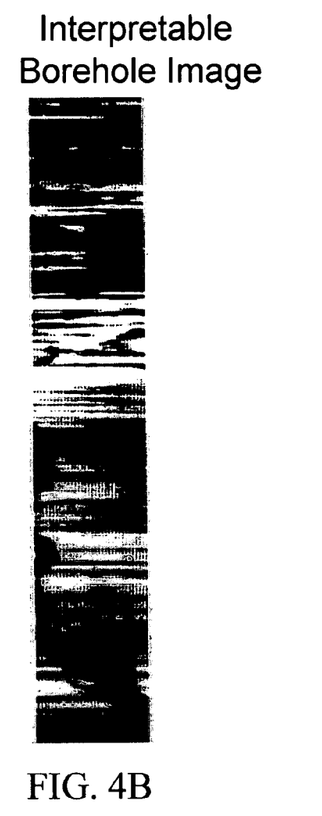

The wireline data, including the borehole image data of step 130, is preferably processed into a digital file containing an interpretable borehole image covering the interval of stratigraphic interest. FIG. 4A shows a short segment, i.e., five feet of a much longer interval of borehole image data. This data is displayed as traces in FIG. 4A. FIG. 4B shows these traces converted to an interpretable borehole image. This conversion is readily performed by commercially available software, such as Recall™ software available from Petris Technology, Inc. of Houston, Tex. Alternative commercial software to create interpretable borehole images is available from vendors such as Schlumberger, Crocker Data Processing, TerraSciences and Techsia. Preferably, the image of the entire interval of stratigraphic interest is contained within a single data file. Although less preferred, the interval could be contained on multiple adjacent data files.

Step 145: (Optional) Plotting the Interpretable Borehole Images

Although not shown on the flowchart of FIG. 2, the digital file of the interpretable borehole image of step 140 is preferably plotted along side conventional well log data onto a long continuous piece of paper to create a plot of interpretable borehole images for the interval of stratigraphic interest in the wellbore. It has been found that examination using the long continuous piece of paper is advantageous over using a computer workstation when examining the interpretable borehole image or images.

Step 150: Creating a Catalogue of Geologic Image Facies

The detailed graphic core description of step 120 is compared to the plot of the interpretable borehole image of step 140 for the same depth interval as the cored interval of step 110. Key features and attributes are identified in the interpretable borehole image. Non-limiting examples of features and attributes may include bedding, layering, image color, dipping or inclined surfaces, etc.

As a result, definitions of geologic image facies are created in the interpretable borehole image for the cored interval. For the purposes of this specification, the term "geologic image facies" shall refer to a geologic classification of intervals from interpretable borehole image into categories (facies). These categories are based on attributes including image color, image texture and patterns, physical structures and other features visible in interpretable borehole images.

Figure 5:
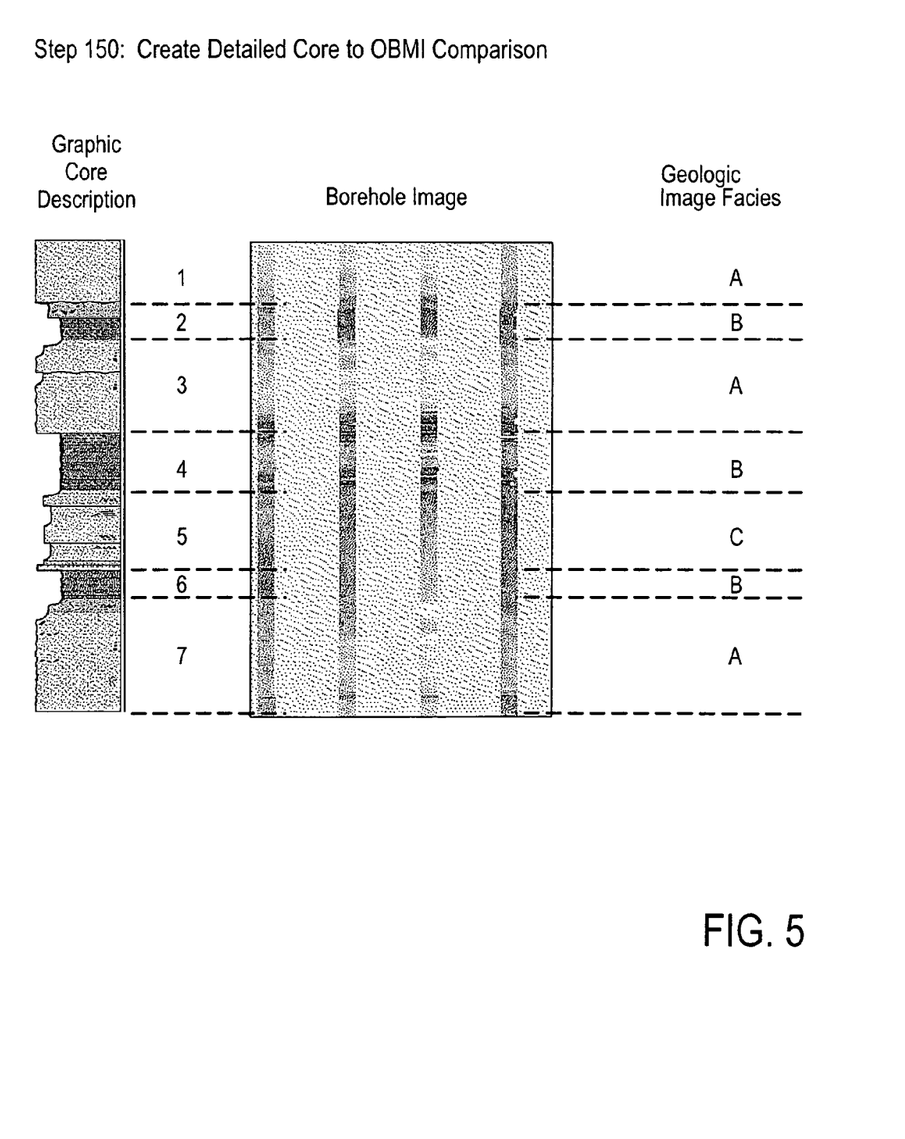
FIG. 5 shows exemplary geologic image facies A, B, and C generated from a graphic core description and a borehole image.

Referring to FIG. 5, intervals 1-7 are identified from the graphic core description. Segments of the borehole image that correspond to these intervals 1-7, are defined as geologic image facies A, B, and C. For example, facies A is massive sandstone and occurs in intervals 1, 3 and 7. Facies B is shale and occurs in intervals 2, 4 and 6. Facies C is bedded sandstone and occurs in interval 5. Consequently, a catalogue of geologic image facies is defined to translate image character into geologic interpretation.

Figure 6:
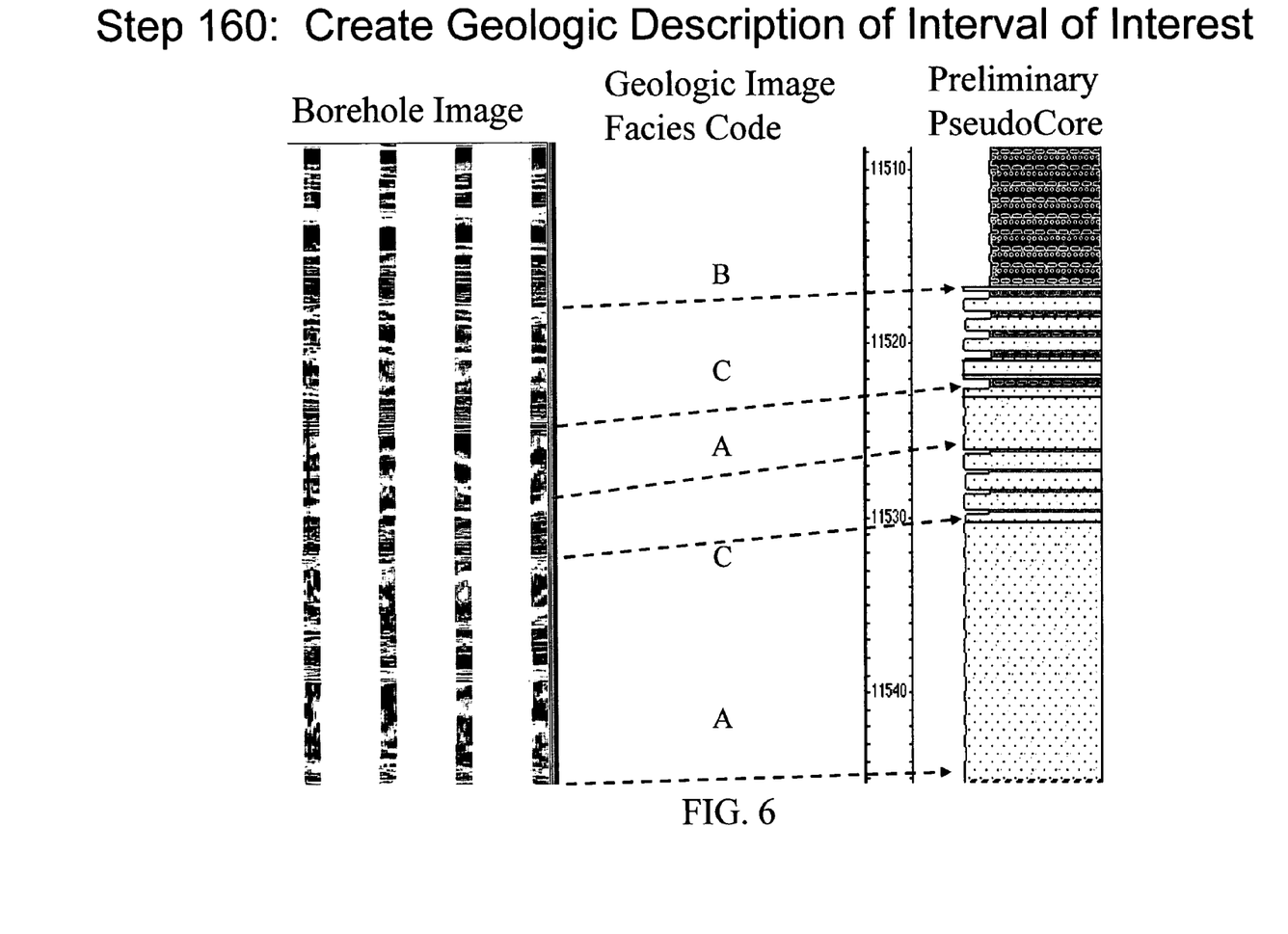
FIG. 6 depicts the conversion of a borehole image into a graphic geologic description referred to as a "pseudocore".

Step 160: Assigning Geologic Image Facies in the Remainder of the Interval of Stratigraphic Interest Referring to FIG. 6, a borehole image is shown on the left. Geologic image facies are assigned to the entire interval of interest of the borehole image using the catalogue established in step 150. For example, the top interval is shale and is assigned facies B. The next interval is assigned with facies C and so on. A graphical representation of the entire succession of geologic image facies is created using geologic patterns to represent each image facies. This graphical representation is referred to as a preliminary "pseudocore" and is shown on the right side in FIG. 6.

Step 170: Creating a Master Pseudocore Interpretation

The interpretable borehole image from step 140, for the entire of interval of stratigraphic interest, is interactively examined using a computer workstation with commercially available image viewing software, such as Petris' Recall. This step preferably includes interactively changing the vertical scale and dynamic color scaling of the images to emphasis subtle features. Furthermore, the software is ideally used to measure and record dipping bed surfaces and to identify faults and other structural features. Subsequently, the geologic description of the borehole images (pseudocore) of the entire interval of interest in the cored well in 160 is updated with the additional analysis to create a master pseudocore for all intervals of interest in the wellbore.

Step 180: Obtaining Second Wireline Data

Wireline data is obtained from a second wellbore covering a second interval of stratigraphic interest. This second wireline data again includes a borehole image, and preferably, a suite of conventional well logs as described in step 130.

Step 190: Processing Second Wireline Data

This second wireline data is then processed into a second interpretable borehole image. The second wireline data may or may not include a portion corresponding to a cored interval. If a core and core interval are available, this core and cored interval are available to enhance the catalogue of geologic image facies.

Step 200: Creating a Second Preliminary Pseudocore

The second borehole image is compared to the existing catalogue of geologic image facies. As a result, a second preliminary pseudocore is created for the second interval of stratigraphic interest.

Step 210: Creating a Second Master Pseudocore

The second interpretable borehole image is interactively examined and compared with the second preliminary pseudocore. As a result, a second master pseudocore is developed for the second interval of stratigraphic interest. This second master pseudocore is created in a manner similar to that described above with respect to step 170.

Step 220: Correlating the Master Pseudocores from the Wellbores to Create a 3-Dimensional Stratigraphic Model:

Referring again to FIG. 1, zones of similar character in the master pseudocores are correlated between wellbores. This correlation is accomplished by recognizing facies or groups of facies that occur in the same vertical order in adjacent wells. As a simple example, a series of a facies A-C-B in one wellbore may be correlated with a similar set of facies A-C-B in another wellbore. Of course, actual geology is typically much more complex. However, the basic principles of correlating corresponding stratigraphic intervals are still applied. The geologic character represented in the pseudocores enables more precise stratigraphic correlation than is possible using conventional wireline log data without interpreted borehole images.

Step 230: Building a Reservoir Model from the Stratigraphic Model;

Subsequently, from the stratigraphic model or interpretation of step 220, a reservoir model may be constructed. This is accomplished by utilizing the correlated zones of similar character from step 220 as input for constructing 3-D reservoir bodies using commercially available software. This software may include GOCAD, or PETREL by Schlumberger Geoquest.

In the event that additional cores are available, these cores may be used to further define or improve the detailed comparisons of core character to interpretable borehole images performed in step 160. These improved detailed comparisons can be applied to all intervals of interest in the master pseudocore interpretations of step 200.

While in the foregoing specification this invention has been described in relation to certain preferred embodiments thereof, and many details have been set forth for purpose of illustration, it will be apparent to those skilled in the art that the invention is susceptible to alteration and that certain other details described herein can vary considerably without departing from the basic principles of the invention.

What is claimed is:

1. A method for creating a stratigraphic model comprising the steps of:
   a) obtaining a core from a wellbore, the wellbore having an interval of stratigraphic interest including a cored interval from which the core was obtained;
   b) examining the core and creating a graphic core description from the core;
   c) obtaining wireline data, including a borehole image, over an interval of stratigraphic interest which contains the cored interval;
   d) processing the wireline data into an interpretable borehole image;
   e) comparing the detailed graphic core description with a portion of the borehole image corresponding to the cored interval to create a catalogue of geologic image facies;
   f) comparing the borehole image to the catalogue of geologic image facies to create a preliminary pseudocore for the interval of stratigraphic interest;
   g) examining the interpretable borehole image and the preliminary pseudocore to create a master pseudocore interpretation;
   h) obtaining a second wireline data from a second wellbore covering a second interval of stratigraphic interest, the second wireline data including a second borehole image;

i) processing the second wireline data into a second interpretable borehole image;

j) comparing the second borehole image to the catalogue of geologic image facies to create a second preliminary pseudocore for the second interval of stratigraphic interest;

k) examining the second interpretable borehole image and the second preliminary pseudocore to create a second master pseudocore; and l) correlating between the first and second master pseudocores of the wellbores to create a stratigraphic model.

2. The method of claim 1 further comprising the step of:
building a reservoir model from the stratigraphic model.

3. The method of claim 1 further including the step of:
using at least one other core obtained from one of the first and second wellbores to enhance the catalogue of geologic image facies prior to the creation of any preliminary pseudocore.

4. The method of claim 3 wherein:
the at least one other core is obtained from the first wellbore.

5. The method of claim 3 wherein:
the at least one other core is obtained from the second wellbore.

6. The method of claim 1 wherein:
the stratigraphic model is three-dimensional.

7. The method of claim 1 wherein:
the stratigraphic model is two-dimensional.

8. The method of claim 1 wherein:
step (e) includes plotting a digital file of the interpretable borehole image on to paper.

9. The method of claim 1 wherein;
the wireline data includes a suite of wellbore logs.

10. The method of claim 9 wherein:
the suite of wellbore logs includes at least one of gamma ray, density, sonic, neutron, caliper, and porosity logs.

11. A method for creating a detailed stratigraphic interpretation of for an uncored wellbore comprising:

a) obtaining a core from a wellbore, the wellbore having an interval of stratigraphic interest including a cored interval from which the core was obtained;

b) examining the core and creating a graphic core description from the core;

c) obtaining wireline data, including a borehole image, over an interval of stratigraphic interest which contains the cored interval;

d) processing the wireline data into an interpretable borehole image;

e) comparing the detailed graphic core description with a portion of the borehole image corresponding to the cored interval to create a catalogue of geologic image facies;

f) comparing the borehole image to the catalogue of geologic image facies to create a preliminary pseudocore for the interval of stratigraphic interest;

g) examining the interpretable borehole image and the preliminary pseudocore to create a master pseudocore interpretation;

h) obtaining a second wireline data from a second uncored wellbore covering a second interval of stratigraphic interest, the second wireline data including a second borehole image;

i) processing the second wireline data into a second interpretable borehole image;

j) comparing the second borehole image to the catalogue of geologic image facies to create a second preliminary pseudocore for the second interval of stratigraphic interest; and k) examining the second interpretable borehole image and the second preliminary pseudocore to create a second master pseudocore for the uncored wellbore to create stratigraphic information based in part from the core of the other wellbore.

* * * * *